United States Patent [19]

Gall

[11] 4,020,085
[45] Apr. 26, 1977

[54] 1-(α-AMINO-α-PHENYL-O-TOLYL-)IMIDAZOLES

[75] Inventor: Martin Gall, Kalamazoo, Mich.

[73] Assignee: The Upjohn Company, Kalamazoo, Mich.

[22] Filed: Apr. 28, 1976

[21] Appl. No.: 681,184

Related U.S. Application Data

[62] Division of Ser. No. 475,459, June 3, 1974, Pat. No. 3,970,666.

[52] U.S. Cl. .............................................. 260/309
[51] Int. Cl.$^2$ ............... C07D 233/64; C07D 233/58
[58] Field of Search .................................... 260/309

[56] References Cited

UNITED STATES PATENTS

| | | | |
|---|---|---|---|
| 3,657,269 | 4/1972 | Houlihan | 260/309.6 |
| 3,763,179 | 10/1973 | Gall | 260/309 |
| 3,772,317 | 11/1973 | Hester | 260/308 R |
| 3,915,981 | 10/1975 | Nakanishi et al. | 260/309 |

OTHER PUBLICATIONS

Chemical Abstracts, Chemical Substance Index, (dib-Peo) 1975, vol. 82, p. 2191CS, col. 3, 5th entry.
Chemical Abstracts, 1975, vol. 82, No. 125376b.

*Primary Examiner*—Natalie Trousof
*Attorney, Agent, or Firm*—Ward F. Nixon; John T. Reynolds

[57] ABSTRACT

3-Substituted 4-(α-amino-α-phenyl-o-tolyl)-4H-1,2,4-triazoles, 2-substituted 1-(αamino-α-phenyl-o-tolyl-)imidazoles, pharmacologically acceptable acid addition salts thereof and processes for their production. The compounds of this invention and the pharmacologically acceptable acid addition salts thereof are useful as sedatives, hypnotics, anticonvulsants, tranquilizers, and muscle relaxants. They are also useful as feed additives for increasing growth rate and feed efficiency of livestock and poultry.

6 Claims, No Drawings

1-(α-AMINO-α-PHENYL-O-TOLYL)IMIDAZOLES

This is a division of application Ser. No. 475,459, filed June 3, 1974, now U.S. Pat. No. 3,970,666.

BACKGROUND OF THE INVENTION

1. Field of the Invention

This invention relates to novel derivatives of benzodiazepines and methods of preparing them. The compounds of this invention are highly active central nervous system depressants.

2. Description of the Prior Art

Related compounds have been previously described, see for example, J. Het. Chem. 8, 181 (1971); Tetrahedron Letters 3869 (1970); and U.S. Pat. No. 3,772,317.

SUMMARY OF THE INVENTION

The novel 3-substituted 4-(α-amino-α-phenyl-o-tolyl)-4H-1,2,4-triazoles of this invention are illustratively represented by generic formula I and the novel 2-substituted 1-(α-amino-α-phenyl-o-tolyl)imidazoles of this invention are illustratively represented by formula II, as follows:

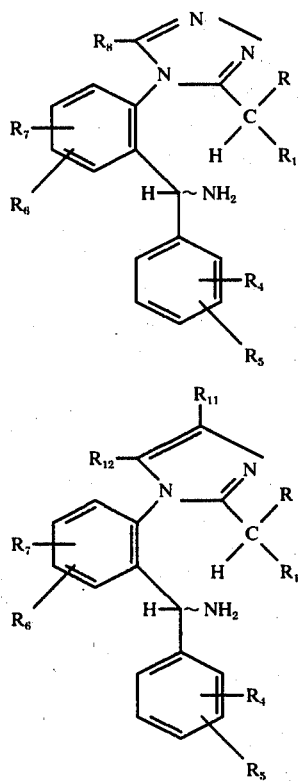

wherein R and $R_1$ taken separately are each hydrogen or when taken together represent a group of the formula:

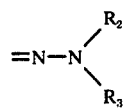

in which $R_2$ is hydrogen or alkyl of 1 to 3 carbon atoms, inclusive i.e., methyl, ethyl, propyl or isopropyl, and $R_3$ is alkyl as defined above; $R_4$, $R_5$, $R_6$ and $R_7$ are each hydrogen, alkyl as defined above, halo, i.e., fluoro, chloro or bromo, nitro or trifluoromethyl; $R_8$ is alkyl as defined above, cyclopropyl, hydroxymethyl, or dialkylaminoalkyl of the formula:

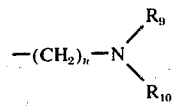

in which $R_9$ and $R_{10}$ are each alkyl as defined above and $n$ is a whole number from 1 to 3, inclusive; and $R_{11}$ is hydrogen, alkyl as defined above, hydroxymethyl or dialkylaminoalkyl as defined above; and $R_{12}$ is hydrogen, alkyl as defined above, cyclopropyl, hydroxymethyl or dialkylaminoalkyl as defined above.

In this application the wavey line (~) appearing in the formulas between the carbon, and the amino group indicates that the compounds of this invention exist in two diastereomeric forms hereinafter identified as the diastereomers A and B (isomer A and isomer B), provided that $R_8$ is not methyl when R and $R_1$ are hydrogen. In the latter case the two diastereomers forms are equivalent to one another and the compounds exist as a racemic mixture.

The invention further embraces the pharmacologically acceptable addition salts of the compounds of formulas I and II, above.

The more desirable compounds of this invention are represented by the following formulas:

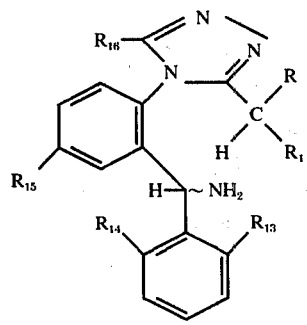

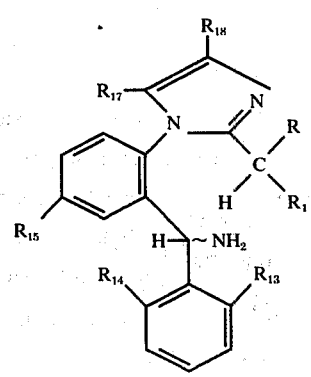

wherein R, and $R_1$ have the meaning previously given; $R_{13}$, $R_{14}$ and $R_{15}$ are each hydrogen, chloro or fluoro; $R_{16}$ is alkyl as defined above, cyclopropyl, hydroxymethyl or dialkylaminomethyl of the formula

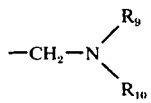

in which $R_9$ and $R_{10}$ have the meanings previously given. $R_{17}$ is hydrogen, alkyl as defined above, hydroxymethyl or dialkylaminomethyl as defined above, and $R_{18}$ is hydrogen, alkyl as defined above, hydroxymethyl or dialkylaminomethyl as defined above; and the pharmacologically acceptable acid addition salts thereof.

The most desirable compounds of this invention are represented by the following formulas:

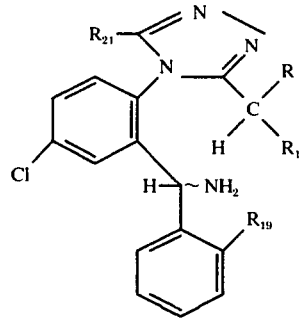

IB

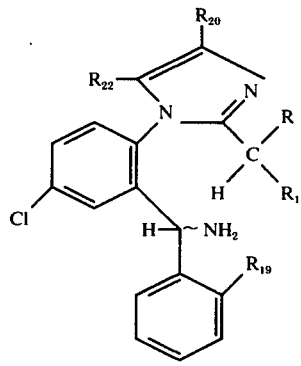

IIB wherein R, and $R_1$ have the meanings previously given, $R_{19}$ is hydrogen or chloro; $R_{20}$ is hydrogen or alkyl as previously defined, $R_{21}$ is alkyl as defined above, cyclopropyl, hydroxymethyl or dimethylaminomethyl; $R_{22}$ is hydrogen, alkyl as defined above, hydroxymethyl or dimethylaminomethyl; and the pharmacologically acceptable acid addition salts thereof.

The novel compounds of this invention as represented by formulas I, II, IA, IIA, 1B and 11B, above, exist in either the non-protonated (free base) form or in the protonated (acid addition salt) form, depending on the pH of the environment. They form stable protonates, i.e., pharmacologically acceptable acid addition salts, on acidification of the free base with suitable pharmacologically acceptable acids, for example, hydrochloric, hydrobromic, sulfuric, phosphoric, nitric, acetic, propionic, palmitic, benzoic, salicylic, hexynoic, phenylbutyric, naphthoic, glycolic, succinic, nicotinic, tartaric, maleic, malic, pamoic, methanesulfonic, cyclohexanesulfonic, citric, and lactic acids, and the like. Conversely, the free bases of the novel compounds of formulae I, II, IA, IIA, IB and IIB can be obtained from a salt, (e.g., from the hydrochloride or sulfate salt) by neutralization with a base such as sodium hydroxide, extracting with an immiscible solvent, for example chloroform, drying the extract, for example with anhydrous sodium sulfate, and removing the solvent by evaporation.

The novel compounds of formulae I, II, IA, IB, and IIB and the pharmacologically acceptable acid addition salts thereof have sedative, hypnotic, anticonvulsant, tranquilizing and muscle relaxant effects in mammals and birds, and as feed additives for increasing the growth rate and feed efficiency of livestock and poultry, milk production during lactation in the mammalian species and egg production in the avian species.

The pharmaceutical forms contemplated by this invention include pharmaceutical compositions suited for oral, parenteral and rectal use, e.g., tablets, powder packets, chachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like are used as carriers or for coating purposes. Water or oils, e.g., coconut oil, sesame oil, safflower oil, cottonseed oil, peanut oil is used for preparing solutions or suspensions of the active drug. Sweetening, coloring, and flavoring agents can be added.

For mammals and birds, food premixes, with starch, oatmeal, dried fishmeat, fishmeal, flour and the like are prepared. These are then incorporated into an animal feed.

As feed additives the compounds of formulae I, II, IA, IIA, IB and IIB are used in dosages of 1 mg. to 100 mg./animal/day in a feed to increase growth, feed consumption and feed efficiency in livestock and poultry, milk production in the mammalian species and egg production in avian species.

As tranquilizers the compounds of Formulae I, II, IA, IIA, IB and IIB are used in unit dosages of 1 mg. to 100 mg. in oral or injectable preparations as described above, to alleviate tension and anxiety in mammals, or birds, such as e.g., occurs when animals are transported.

The novel compounds of this invention are prepared in accordance with the following reaction sequences:

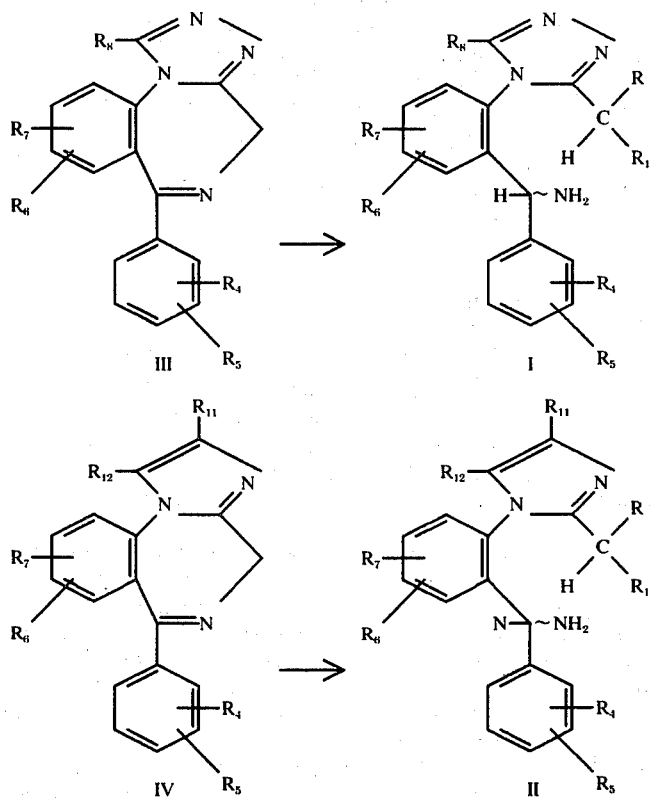

wherein R, $R_1$, $R_4$, $R_5$, $R_6$, $R_7$, $R_8$, $R_{11}$ and $R_{12}$ have the meanings previously given.

The starting materials of formulas III and IV of this invention are known in the art.

In carrying out the process for the production of the novel compounds of this invention which are included within the scope of formulas I and II above, the selected starting material is reacted with hydrazine or an alkyl or dialkyl hydrazine of the formula:

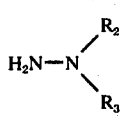

in which $R_2$ and $R_3$ have the meanings previously given, for example methyl hydrazine, ethyl hydrazine, propyl hydrazine, isopropyl hydrazine, dimethyl hydrazine, diethyl hydrazine, dipropyl hydrazine, diisopropyl hydrazine, methyl ethyl hydrazine, methyl propyl hydrazine, methyl isopropyl hydrazine, ethyl propyl hydrazine, ethyl isopropyl hydrazine and propyl isopropyl hydrazine, and the like. The reaction is carried out by reacting the selected starting triazole III or imidazole IV with hydrazine or the appropriate alkyl or dialkyl hydrazine in a relatively high boiling solvent, preferably a protic solvent such as a glycol, e.g., diethylene glycol, ethylene glycol, propylene glycol and the like. The reaction is carried out within a temperature range of from about 90° C. to about 200° C. for a period of from about 1 to about 48 hours. A temperature within the range of from about 120° C. to about 160° C. is preferred. The time required for the reaction depends in part on the particular reactants and the temperature employed; a period of from about 1 to 24 hours is generally sufficient for completion of the reaction. It is to be understood that when hydrazine hydrate is used the compounds of formulas I and II wherein $R_1$ and $R_2$ are each hydrogen are obtained and when an alkyl or dialkyl hydrazine is used the compounds of formulas I and II wherein R and $R_1$ together represent a group of the formula

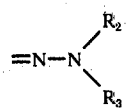

are obtained. The compounds of formula I and II thus obtained are recovered from the reaction mixture and purified by conventional methods, for example by crystallization from a suitable organic solvent such as benzene, toluene, chloroform, methylene chloride, ethyl acetate, hexanes, mixtures thereof and the like or by chromatography on silica gel followed by crystallization from a suitable organic solvent such as those named above.

The process and products of this invention are further illustrated by the following specific examples.

EXAMPLE 1

4-[α-Amino-4-chloro-α-(o-chlorophenyl)-o-tolyl]-3,5-dimethyl-4H-1,2,4-triazole (I)

A solution of 1.372 g. (4.00 mmol.) of 8-chloro-6-(o-chlorophenyl)-1-methyl-4H-s-triazolo[4,3-a][1,4]benzodiazepine (III) and 1.00 ml. of 99% hydrazine hydrate in 7.5 ml. of diethylene glycol is heated to 140° C. for about 20 hours. (The reaction is completed after 3 hours). The reaction mixture is then quenched in a 5% aqueous sodium hydroxide solution and the products are extracted with chloroform, dried over magnesium sulfate and concentrated in vacuo to give an oil. Crystallization of the oil thus obtained from ethyl acetate gives 450 mg. of fine white needles of 4-[α-amino-4-chloro-α-(o-chlorophenyl)-o-tolyl]-3,5-dimethyl-4H-1,2,4-triazole (I) as a racemic mixture m.p. 177°–178° C.; a sample recrystallized from an ethyl acetate/hexane mixture gives the analytical sample of racemate, m.p. 192°–193° C., infrared (mull) spectral absorptions at 3360, 3280, 1590, 1565, 1530 and 1490 $cm^{-1}$.

Anal. Calcd for $C_{17}H_{18}Cl_2N_4$, m.w. 347.24: C 58.80; H 4.65; N 16.14; Cl 20.42. Found: C 58.79; H 4.69; N 16.33; Cl 20.29.

EXAMPLE 2

4-[α-Amino-4-chloro-α-(o-chlorophenyl)-o-tolyl]-3-cyclopropyl-5-methyl-4H-1,2,4-triazole (I) isomers A and B A solution of 1.477 g. (4.00 mmol.) of 8-chloro-6-(o-chlorophenyl)-1-cyclopropyl-4H-s-triazolo[4,3-a][1,4]benzodiazepine (III) and 1.00 ml. of hydrazine hydrate in 7.5 ml. of diethylene glycol is heated to 140° C. for about 6 hours and cooled to room temperature. The reaction mixture is then quenched in a 5% aqueous sodium hydroxide solution and the products are extracted with chloroform, dried over anhydrous magnesium sulfate and concentrated in vacuo to give an oil. The oil thus obtained is chromatographed over 150 g. of silica gel eluting wth a methanol/chloroform (3/97) solution; 10 ml. fractions are collected. The fractions which are shown by TLC (thin layer chromatography) to contain isomer A are combined and crystallized from ethyl acetate/-hexane mixtures to give 140 mg. of 4-[α-amino-4-chloro-α-(o-chlorophenyl)-o-tolyl]-3-cyclopropyl-5-methyl-4H-1,2,4-triazole (I), isomer A, as a solvate, melting at 50°–70° C., which solidified and remelted at 140°–145° C.; and analytical sample of which melted at 144°–147° C., and has infrared (mull) spectral absorptions at 3370, 3260, 3180, 1610, 1590, 1570, 1535 and 1485 $cm^{-1}$.

Anal. Calcd for $C_{19}H_{18}Cl_2N_4$, m.w. 373.27: C 61.13; H 4.86; N 15.01; Cl 18.99. Found: C 61.30; H 4.93; N 15.27; Cl 18.94;

The fractions which were shown by TLC to contain isomer B are combined and crystallized to give 720 mg. of 4-[α-amino-4-chloro-α-(o-chlorophenyl)-o-tolyl]-4H-1,2,4-triazole (I), isomer B; m.p. 170°–172° C.; infrared (mull) spectral absorptions at 3370, 3300, 3050, 1590, 1570, 1530 and 1485 $cm^{-1}$.

Anal. Calcd for $C_{19}H_{18}Cl_2N_4$, m.w. 373.27: C 61.13; H4.86; N 15.01; Cl 18.99; Found: C 61.12; H 4.89; N 15.11; Cl 19.03.

EXAMPLE 3

4-[α-Amino-4-chloro-α-(o-chlorophenyl)-o-tolyl]-5-methyl-4H-1,2,4-triazole-3-carboxaldehyde, methylhydrazone (I), mixture of isomers A and B A solution of 1.372 g. (4.00 mmol.) of 8-chloro-6-(o-chlorophenyl)-1-methyl-4H-s-triazolo[4,3-a][1,4]benzodiazepine (III) and 1.00 ml. of 99% methyl hydrazine in 7.5 ml. of diethylene glycol is heated to 140° C. for about 17 hours. The reaction mixture is quenched in an aqueous 5% sodium hydroxide solution, extracted with chloroform, dried (sodium sulfate) and concentrated in vacuo to give an oil. The oil thus obtained is triturated with ethyl acetate to give 200 mg. of fine white needles of 4-[α-amino-4-chloro-α-(o-chlorophenyl)-o-tolyl]-5-methyl-4H-1,2,4-triazole-3-carboxaldehyde, methylhydrazone (I), as a mixture of diastereomers A and B, m.p. 175°–185° C.; an analytical sample of which melted at 173°–184° C., and has infrared (mull) spectral absorptions at 3260, 3060, 1600, 1570, 1535 and 1480 $cm^{-1}$.

Anal. Calcd for $C_{18}H_{18}Cl_2N_6$, m.w. 389.28: C 55.53; H 4.66; N 21.59; Cl 18.21. Found: C 55.59; H 4.64; N 22.02; Cl 18.11.

EXAMPLE 4

4-[α-Amino-4-chloro-α-(o-chlorophenyl)-o-tolyl]-5-methyl-4H-1,2,4-triazole-3-carboxaldehyde, dimethylhydrazone (I), isomers A and B A solution of 2.74 g. (8.00 mmol.) of 8-chloro-6-(o-chlorophenyl)-1-methyl-4H-s-triazolo[4,3-a][1,4]benzodiazepine (III) and 3.00 ml. of dimethyl hydrazine in 15 ml. of diethylene glycol is heated to 140°–150° C. for about 17 hours. The reation mixture is quenched in a 5% aqueous sodium hydroxide solution and the products are extracted with chloroform, dried (sodium sulfate) and concentrated in vacuo to give an oil. The oil thus obtained is chromatographed over 200 g. of silica gel and eluted with 2 l. of methanol/-chloroform (3/97). The fractions which are shown by TLC to contain isomer A are combined and crystallized from methanol/ethyl acetate mixtures to give 1.5 g. of 4-[α-amino-4-chloro-α-(o-chlorophenyl)-o-tolyl]-5-methyl-4H-1,2,4-triazole-3-carboxaldehyde, dimethylhydrazone, isomer A, (I); an analytical sample of which melts at 217°–219° C., and has infrared (mull) spectral absorptions at 3350, 3280, 2780, 1530 and 1490 $cm^{-1}$.

Anal. Calcd for $C_{19}H_{20}Cl_2N_6$, m.w. 403.31: C 56.58; H 5.00; N 20.84; Cl 17.58. Found: C 56.41; H 5.05; N 20.84; Cl 17.82.

The fractions which are shown by TLC to contain isomer B are combined and crystallized from methanol-/ethyl acetate mixtures to give 710 mg. of 4-[α-amino-4-chloro-α-(o-chlorophenyl)-o-tolyl]-5-methyl-4H-1,2,4-triazole-3-carboxaldehyde, dimethylhydrazone, isomer B, (I); an analytical sample of which melts at 197.5°–198.5° C. and has infrared (mull) spectral absorptions at 3350, 3280, 2780, 1595, 1530 and 1485 $cm^{-1}$.

Anal. Calcd for $C_{19}H_{20}Cl_2N_6$, m.w. 403.31: C 56.58; H 5.00; N 20.84; Cl 17.58; Found: C 56.32; H 4.92; N 20.99; Cl 17.71.

EXAMPLE 5

4-[-α-Amino-4-chloro-α-(o-chlorophenyl)-o-tolyl]-3-[(dimethylamino)methyl]-5-methyl-4H-1,2,4-triazole (I), isomers A and B A solution of 7.38 g. of 8-chloro-6-(o-chlorphenyl)-1-(dimethylamino)methyl-4H-s-triazolo[4,3-a][1,4]benzodizepine (III) (20.0 mmol.) and 5.0 ml. of hydrazine hydrate in 50 ml. of diethylene glycol is heated to about 140° C. for about 18 hours. The reaction is quenched in a cold aqueous 5% sodium hydroxide solution, and the product extracted with chloroform. The extracts are dried and concentrated in vacuo to yield 8.5 g. of oil, which is crystallized from ethyl acetate/hexane mixtures to give 4.0 g. of 4-[α-amino-4-chloro-α-(o-chlorophenyl)-o-tolyl]-3-[(dimethylamino)methyl]-5-methyl-4H-1,2,4-triazole (I), isomer A, m.p. 142°–144° C., an analytical sample of which melts at 148°–150° C. and has infrared (mull) spectral absorptions at 3380, 3270, 3200, 3070, 2770, 1610, 1590, 1570, 1530 and 1520 cm$^{-1}$.

Anal. Calcd for $C_{19}H_{21}Cl_2N_5$, m.w. 390.30: C 58.47; H 5.42; N 17.94; Cl 18.17; Found: C 58.40; H 5.40; N 18.07; Cl 18.27.

Isomer B of 4-[α-amino-4-chloro-α-(o-chlorophenyl)-o-tolyl]-3-[(dimethylamino)methyl]-5-methyl-4H-1,2,4-triazole (I) is recovered from the mother liquors by column chromatography and fractional crystallization.

EXAMPLE 6

4-[α-Amino-4-chloro-α-(o-chlorophenyl)-o-tolyl]-3-hydroxymethyl-5-methyl-4H-1,2,4-triazole (I), isomers A and B A mixture of 10.776 g. 8-chloro-6-(o-chlorophenyl)-1-hydroxymethyl-4H-s-triazolo[4,3-a][1,4]benzodiazepine (111) (30.0 mmoles) and 7.50 ml. of hydrazine hydrate in 60 ml. of diethylene glycol is heated to 150°–160° C. for about 18 hours. The reaction is then quenched in a cold aqueous 5% sodium hydroxide solution and the product extracted with chloroform. The extracts thus obtained are dried over anhydrous magnesium sulfate and concentrated in vacuo to give 13.0 g. of oil which is crystallized from methanol/ethyl acetate to give 1.93 g. of a mixture of the A and B isomers (ratio 81/19) of 4-[α-amino-4-chloro-α-(o-chlorophenyl)-o-tolyl]-3-(hydroxymethyl)-5-methyl-4H-1,2,4-triazole (I) m.p. 205°–215° C. The mixture thus obtained is recrystallized from the same solvent mixture to give 0.76 g. of 4-[α-amino-4-chloro-α-(o-chlorophenyl)-o-tolyl]-o-tolyl]-3-(hydroxymethyl)-5-methyl-4H-1,2,4-triazole (I), (isomer A) melting at 218°– 223° C., and having infrared (mull) spectral absorptions at 3330, 3240, 3150, 3060, 2680, 1600, 1570, 1530, 1515 and 1485 cm$^{-1}$.

Anal. Calcd for $C_{17}H_{18}Cl_2N_4$, m.w. 363.24: C 56.21; H 4.44; N 15.43; cl 19.5. Found: C 56.28; H 4.36; N 15.72; Cl 19.77.

A second crop of 3.85 g. of crystalline product is shown by NMR to be a mixture of A and B isomers (ratio 43/57) which can be selectively crystallized. High pressure liquid chromatography of a 1.0 g. sample gives 80 mg. of 4-[α-amino-4-chloro-α-(o-chlorophenyl)-o-toly]-3-(hydroxymethyl)-5-methyl-4H-1,2,4-triazole (1) isomer B, which when crystallized from ethyl acetate/methanol melts at 225°–229° C. and has infrared (mull) spectral absorptions at 3410, 3340, 3200, 3060, 2630, 1610, 1590, 1580, 1530, 1515 and 1485 cm$^{-1}$.

Anal. Calcd for $C_{17}H_{18}Cl_2N_4$, m.w. 363.24: C 56.21; H 4.44; N 15.43; Cl 19.52. Found: C 56.44; H 4.52; N 15.14; Cl 19.13.

EXAMPLE 7

1-[α-Amino-4-chloro-α-(o-chlorophenyl)-o-tolyl]-2,4-dimethylimidazole (11), mixture of isomers A and B A solution of 1.369 g. (4.00 mmol.) of 8-chloro-6-(o-chlorophenyl)-2-methyl-4H-imidazo[1,2-a][1,4]benzodiazepine (IV) and 1.00 ml. of hydrazine hydrate dissolved in 7.5 ml. of diethylene glycol is heated to 140°–160° C. for about 21 hours and cooled to room temperature. The reaction mixture is then quenched in a 5% aqueous sodium hydroxide solution and the products are extracted with chloroform, dried (magnesium sulfate) and concentrated in vacuo to afford a colorless oil. crystallization of the oil thus obtained from ethyl acetate/hexane mixtures gives 900 mg. (65% yield) of 1-[α-amino-4-chloro-α-(o-chlorophenyl)-o-tolyl]-2,4-dimethyl imidazole (II) m.p. 158°–160° C. A second crop weighed 220 mg. (15.9%). An analytical sample of 1-[α-amino-4-chloro-α-(o-chlorophenyl)-o-tolyl]-2,4-dimethyl-imidazole (II) as a mixture of isomers A and B melts at 159°–161° C. and has infrared (mull) spectral absorptions at 3360, 3270, 3060, 1590, 1565 and 1490 cm$^{-1}$.

Anal. Calcd for $C_{18}H_{17}Cl_2N_3$, m.w. 346.25: C, 62.43; H 4.95; N 12.14; Cl 20.48.

Found: C 62.34; H 5.01; N 12.09; Cl 20.35.

EXAMPLE 8

1-(α-Amino-4-chloro-α-phenyl-o-tolyl)-2-methylimidazole, hydorbromide (II), isomers A and B A solution of 13.69 g. (46.5 mmol.) of 8-chloro-6-phenyl-4H-imidazo[1,2-α][1,4]benzodiazepine (IV) and 10 ml. of hydrazine hydrate in 75 ml. of dietylene glycol is heated to 130°–160° C. for about 24 hours. The reaction mixture is cooled and quenched in a 5% aqueous sodium hydroxide solution and the products are extracted with chloroform, dried over sodium sulfate and concentrated in vacuo to give a oil. The oil this obtained is chromatographed over 500 g. of silica gel by eluting with 3 l. of a methanol/chloroform solution (3/97) and 2 l. of a 5/95 mixture of the same two solvents. Fractions which are shown to contain the desired product by TLC are combined and concentrated in vacuo to give 6.3 g. of 1-(α-amino-4-chloro-α-phenyl-o-tolyl)-2-methylimidazole as an oil which is crystallized as the hydrobromide salt to give 2.29 g. of 1-(α-amino-4-chloro-α-phenyl-o-tolyl)-2-methylimidazole hydrobromide (II), as a mixture of isomers A and B, melting at 297°–300° C. and having infrared (mull) spectral absorptions at 2660, 2350 2080, 1625, 1590, 1525 and 1495 cm$^{-1}$.

Anal. Calcd for $C_{17}H_{16}ClN_3$ nHBr m.w. 378.74: C, 53.91; H 4.52; N 11.10; Cl 9.36; Br 21.11.

Found: C 53.83; H 4.56; N 10.96; Cl 9.24; Br 20.70.

EXAMPLE 9

4-[α-Amino-4-chloro-α-(2,6-dichlorophenyl)-o-tlyl]-3,5-dimethyl-4H-1,2,4-triazole (I)

In the manner given in Examples 1–7, above, 8-chloro-6-(2,6-dichlorophenyl)-1-methyl-4H-s-triazole[4,3-a][1,4]-benzodiazepine (III) in diethylene glycol is treated with hydrazine hydrate to obtain 4-[α-amino-4-chloro-α-(2,6-dichlorophenyl)-o-tolyl]-3,5-dimethyl-4H-1,2,4-triazole (I).

EXAMPLE 10

4-[α-Amino-4-chloro-2-(2,6-difluorophenyl)-o-tolyl]-3,5-dimethyl-4H-1,2,4-triazole (I)

In the manner given in Examples 1–7, 8-chloro-6-(2,6-difluorophenyl)-1-methyl-4H-s-triazolo[4,3-a][1,4]benzodiazepine (III) in diethylene glycol is treated with hydrazine hydrate to obtain 4-[α-amino-4- chloro-2-(2,6-difluorophenyl)-o-tolyl]-3,5-dimethyl-4H-1,2,4-triazole (I).

EXAMPLE 11

4-α-Amino-α-phenyl-o-tolyl]-5-ethyl-4H-1,2,4-triazole-3-carboxaldehyde, propylhydrazone, isomers A and B In the manner given in Examples 1–7, above, 1-ethyl-6-phenyl-4H-s-triazolo[4,3-α][1,4]benzodiazepine (III) in diethylene glycol is treated wit propyl hydrazine to obtain both A and B 4-[α-amino-α-phenyl-o-tolyl]-5-ethyl]-4H-1,2,4-triazole-3-carboxaldehyde, propylhydrazone, which is separated by column chromatography into the two diastereomers A and B.

EXAMPLE 12

1-(α-Amino-4-chloro-α-phenyl-o-tolyl)-2-methyl-5-[(dimethylamino)methyl]imidazole (II), isomers A and B In the manner given in Examples 1–7, above, 8-chloro-1-dimethylaminomethyl-6-phenyl-4H-imidazo[1,2-a][1,4]benzodiazepine (IV) in diethylene glycol is treated with hydrazine hydrate to obtain both A and B 1-(α-amino-4-chloro-α-phenyl-o-tolyl)-2-methyl-5-[(dimethylamino)-methyl]imidazole (II) which is separated by column chromatography and fractional crystallization into the two diastereomers A and B.

EXAMPLE 13

1-[α-Amino-4-chloro-α-(o-chlorophenyl)-o-tolyl]-2-methyl-5-dimethylaminomethyl imidazole (II), isomers A and B In the manner given in Examples 1–7, above, 8-chloro-6-(o-chlorophenyl)1-dimethylaminomethyl-4H-imidazo[1,2-a]-[1,4]benzodiazepine (IV) in diethylene glycol is treated wit hydrazine hydrate to obtain A and B 1-[α-amino-4-chloro-α-(o-chlorophenyl)-o-tolyl]-2-methyl-5-dimethyl-aminomethyl imidazole (II) which is separated by column chromatography and fractional crystallization into the two diastereomers A and B.

EXAMPLE 14

1-[α-Amino-4-chloro-α-(o-chlorophenyl-o-tolyl-]imidazole-2-carboxaldehyde, diethyl-hydraxone (II), isomers A and B In the manner given in Examples 1–7, above, 8-chloro-6-(o-chlorophenyl)-4H-imidazo[1,2-a][1,4]benzodiazepine (IV) in diethylene glycol is treated with diethyl hydrazine to obtain A and B 1-[α-amino-4-chloro-α-(o-chlorophenyl)-o-tolyl]imidazo-2-carboxaldehyde, diethylhydrazone (II) which is separated by column chromatography and fractional crystallization into the two diastereomers A and B.

Following the procedures of Examples 1–7, above, other compounds of formulas III and IV are reacted with hydrazine hydrate, a monoakylhydrazine, or a dialkyl hydrazine to obtain the corresponding compounds of formulas I and II, such as 4-(α-amino-4-chloro-α-phenyl-o-tolyl)-3,5-dimethyl-4H-1,2,4-triazole (I); 4-(α-amino-4-chloro-α-phenyl-o-tolyl)-5-methyl-4H-1,2,4-triazolo-3-carboxaldehyde, dimethyl-hydrazone I, isomers A and B; 1-(α-amino-4-chloro-α-phenyl-o-tolyl)-4-methyl imidazole-2-carboxaldehyde dimethylhydrazone (II), isomers A and B; and the like.

I claim:
1. A compound of the formula:

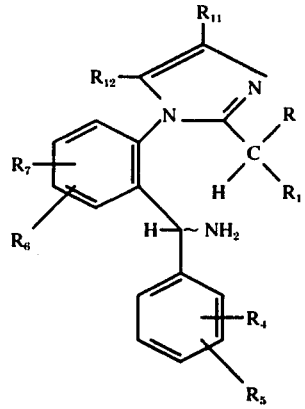

wherein R and $R_1$ taken separately are each hydrogen or when taken together represent a group of the formula:

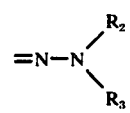

in which $R_2$ is hydrogen or alkyl of 1 to 3 carbon atoms, inclusive and $R_2$ is alkyl as defined above; $R_4$, $R_5$, $R_6$, and $R_7$ are each hydrogen, alkyl as defined above, halo, nitro or trifluormethyl; $R_{11}$ is hydrogen, alkyl as defined above, hydroxymethyl, or a dialkylaminoalkyl of the formula:

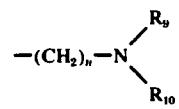

in which $R_2$ and $R_{10}$ are each alkyl as defined above and $n$ is a whole number from 1 to 3, inclusive; and $R_{12}$ is hydrogen, alkyl as defined above, cyclopropyl, hydroxymethyl or dialkylaminoalkyl as defined above; and the pharmacologicaly acceptable acid addition salts thereof.

2. A compound according to claim 1 of the formula:

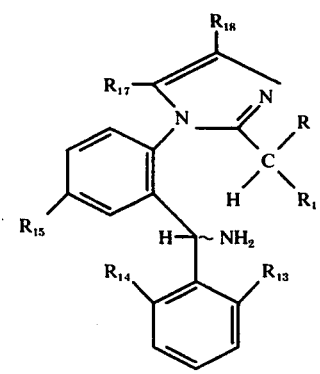

wherein R and R₁ taken separately are each hydrogen or when taken together represent a group of the formula:

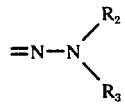

in which $R_2$ is hydrogen or alkyl of 1 to 3 carbon atoms, inclusive, and $R_3$ is alkyl as defined above; $R_{15}$, $R_{14}$ and $R_{15}$ are each hydrogen, chloro or fluoro; $R_{17}$ is hydrogen, alkyl as defined above, hydroxymethyl or dialkylamino-methyl of the formula

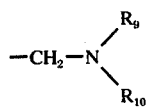

in which $R_9$ and $R_{10}$ are each alkyl as defined above and $R_{16}$ is hydrogen, alkyl as defined above, hydroxymethyl, or dialkylaminomethyl as defined above; and the pharmacologically acceptable acid addition salts thereof.

3. A compound according to claim 1 of the formula:

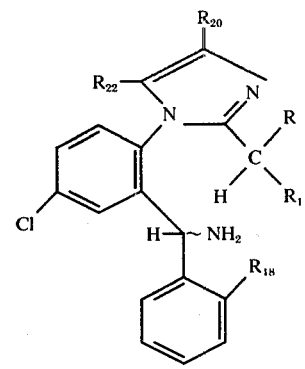

wherein R and R₁ taken separately are each hydrogen or when taken together represent a group of the formula:

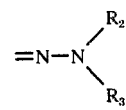

in which $R_2$ is hydrogen or alkyl of 1 to 3 carbon atoms, inclusive, and $R_3$ is alkyl as defined above; $R_{19}$ is hydrogen or chloro; $R_{20}$ is hydrogen or alkyl as defined above; $R_{22}$ is hydrogen, alkyl as defined above, hydroxymethyl, or dimethylaminomethyl; and the pharmacologically acceptable acid addition salts thereof.

4. 1-[α-amino-4-chloro-α-(o-chlorophenyl)0-tolyl]-2,4-dimethylimidazole, the compound according to claim 3, wherein $R_1$, $R_2$ and $R_{22}$ is each hydrogen, $R_{19}$ is chloro, and $R_{20}$ is methyl.

5. 1-(α-amino-4-chloro-α-phenyl-o-tolyl)-2-methylimidazole hydrobromide, the compound of claim 3 wherein R and R₁ are each hydrogen; $R_{19}$, $R_{20}$, and $R_{22}$ are ech hydrogen, and the pharmacologically acceptable acid addition salt is the hydrobromide.

6. 1-(α-amino-4-chloro-α-phenyl-o-tolyl)-2-methyl-5-[(dimethylamino)methyl]imidazole, the compound of claim 3, wherein R and R₁, $R_{19}$ and $R_{20}$ are each hydrogen and $R_{22}$ is dimethylaminomethyl.

* * * * *

UNITED STATES PATENT AND TRADEMARK OFFICE
CERTIFICATE OF CORRECTION

PATENT NO. : 4,020,085
DATED : April 26, 1977
INVENTOR(S) : Martin Gall

It is certified that error appears in the above-identified patent and that said Letters Patent are hereby corrected as shown below:

Abstract, line 2; change "($\alpha$amino-..." to --($\alpha$-amino-... --.

Column 12, line 33; change "$R_2$" to --$R_3$--.

Column 12, line 44; change "$R_2$" to --$R_9$--.

Column 13, line 19; change "$R_{15}$, $R_{14}$ and $R_{15}$" to --$R_{13}$, $R_{14}$ and $R_{15}$--.

Column 13, line 38; change "$R_{16}$" to --$R_{18}$--.

Column 14, line 27; change "$R_2$" to --$R_3$--.

Column 14, line 39; change "ech" to --each--.

Signed and Sealed this

First Day of July 1980

[SEAL]

Attest:

SIDNEY A. DIAMOND

*Attesting Officer*   *Commissioner of Patents and Trademarks*